(12) United States Patent
Matsuyama

(10) Patent No.: US 8,183,342 B2
(45) Date of Patent: May 22, 2012

(54) METHOD OF TREATING CHEMOTHERAPY-INDUCED THROMBOCYTOPENIA

(75) Inventor: Shigemi Matsuyama, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 510 days.

(21) Appl. No.: 12/266,244

(22) Filed: Nov. 6, 2008

(65) Prior Publication Data

US 2009/0118165 A1    May 7, 2009

Related U.S. Application Data

(60) Provisional application No. 60/985,782, filed on Nov. 6, 2007.

(51) Int. Cl.
*C07K 5/10* (2006.01)

(52) U.S. Cl. ...... 530/330; 514/21.8; 514/13.7; 514/21.9
(58) Field of Classification Search .............. 530/330; 514/21.8, 21.9, 13.7
See application file for complete search history.

(56) References Cited

U.S. PATENT DOCUMENTS

| | | | |
|---|---|---|---|
| 5,869,451 A * | 2/1999 | Dower et al. ................. 514/7.8 |
| 2003/0091565 A1* | 5/2003 | Beltzer et al. .............. 424/144.1 |
| 2008/0070840 A1* | 3/2008 | Min et al. ........................ 514/12 |
| 2009/0054342 A1* | 2/2009 | Cohen et al. .................... 514/13 |

* cited by examiner

*Primary Examiner* — David Lukton
(74) *Attorney, Agent, or Firm* — Tarolli, Sundheim, Covell & Tummino LLP

(57) ABSTRACT

A method of treating chemotherapy-induced thrombocytopenia includes administering to a subject undergoing chemotherapy a therapeutically effective amount of a Bax-inhibiting peptide.

9 Claims, 11 Drawing Sheets

METHOD OF TREATING CHEMOTHERAPY-INDUCED THROMBOCYTOPENIA

RELATED APPLICATION

This application claims priority from U.S. Provisional Application No. 60/985,782, filed Nov. 6, 2007, the subject matter, which is incorporated herein by reference.

BACKGROUND

Chemotherapy-induced thrombocytopenia is caused by the decrease of megakaryocytes due to apoptosis of bone marrow stem cells and megakaryocytes (Kaushansky, K., *The thrombocytopenia of cancer. Prospects for effective cytokine therapy*. Hematol Oncol Clin North Am, 1996. 10(2): p. 431-55; Prow, D. and S. Vadhan-Raj, *Thrombopoietin: biology and potential clinical applications*. Oncology (Williston Park), 1998. 12(11): p. 1597-604, 1607-8; discussion 1611-4; Thiele, J., et al., *Effects of the tyrosine kinase inhibitor imatinib mesylate(STI571) on bone marrow features in patients with chronic myelogenous leukemia*. Histol Histopathol, 2004. 19(4): p. 1277-88; Lonial, S., et al., *Risk factors and kinetics of thrombocytopenia associated with bortezomib for relapsed, refractory multiple myeloma*. Blood, 2005. 106(12): p. 3777-84. To reduce thrombocytopenia, treatments aiming to increase stem cell proliferation and megakaryocytes differentiation have been examined. For the differentiation of megakaryocytes from stem cells, interleukins and thrombopoietin (TPO) play important roles (Kaluzhny, Y. and K. Ravid, *Role of apoptotic processes in platelet biogenesis*. Acta Haematol, 2004. 111(1-2): p. 67-77). Early clinical studies of interleukins (ILs) showed that they stimulated the formation of platelets directly or indirectly in patients with chemotherapy-induced thrombocytopenia (Vadhan-Raj, S., et al., *Effects of interleukin-1 alpha on carboplatin-induced thrombocytopenia in patients with recurrent ovarian cancer*. J Clin Oncol, 1994. 12(4): p. 707-14; Leonardi, V., et al., *Interleukin 3 in the treatment of chemotherapy induced thrombocytopenia*. Oncol Rep, 1998. 5(6): p. 1459-64; D'Hondt, V., et al., *Thrombopoietic effects and toxicity of interleukin-6 in patients with ovarian cancer before and after chemotherapy: a multicentric placebo-controlled, randomized phase Ib study*. Blood, 1995. 85(9): p. 2347-53; Gordon, M. S., et al., *A phase I trial of recombinant human interleukin-11 (neumega rhIL-11 growth factor) in women with breast cancer receiving chemotherapy*. Blood, 1996. 87(9): p. 3615-24; Tepler, I., et al., *A randomized placebo-controlled trial of recombinant human interleukin-11 in cancer patients with severe thrombocytopenia due to chemotherapy*. Blood, 1996. 87(9): p. 3607-14; Smith, J. W., 2nd, et al., *The effects of treatment with interleukin-1 alpha on platelet recovery after high-dose carboplatin*. N Engl J Med, 1993. 328(11): p. 756-61). However, the pleiotropic effect of ILs often results in side effects, including hyperbilirubinemia, anemia, fever, hypotension, headaches, and chills (Vadhan-Raj, S., et al., *Effects of interleukin-1 alpha on carboplatin-induced thrombocytopenia in patients with recurrent ovarian cancer*. J Clin Oncol, 1994. 12(4): p. 707-14; Smith, J. W., 2nd, et al., *The effects of treatment with interleukin-1 alpha on platelet recovery after high-dose carboplatin*. N Engl J Med, 1993. 328 (11): p. 756-61; Gordon, M. S., et al., *A phase I trial of recombinant human interleukin-6 in patients with myelodysplastic syndromes and thrombocytopenia*. Blood, 1995. 85(11): p. 3066-76; Lazarus, H. M., et al., *Phase I multicenter trial of interleukin 6 therapy after autologous bone marrow transplantation in advanced breast cancer*. Bone Marrow Transplant, 1995. 15(6): p. 935-42; Nieken, J., et al., *Recombinant human interleukin-6 induces a rapid and reversible anemia in cancer patients*. Blood, 1995. 86(3): p. 900-5). Apoptosis inhibition in megakaryocytes has been examined previously (Srivastava, R. K., et al., *Involvement of microtubules in the regulation of Bcl2 phosphorylation and apoptosis through cyclic AMP-dependent protein kinase*. Mol Cell Biol, 1998. 18(6): p. 3509-17; Yin, D. X. and R. T. Schimke, *BCL-2 expression delays drug-induced apoptosis but does not increase clonogenic survival after drug treatment in HeLa cells*. Cancer Res, 1995. 55(21): p. 4922-8; Biswas, R. S., et al., *Inhibition of drug-induced Fas ligand transcription and apoptosis by Bcl-XL*. Mol Cell Biochem, 2001. 225(1-): p. 7-20). Anti-apoptotic proteins such as Bcl-2, Bcl-XL, and caspase inhibitors were shown to be useful for protecting megakaryocytes from apoptosis (Kaluzhny, Y., et al., *BclxL overexpression in megakaryocytes leads to impaired platelet fragmentation*. Blood, 2002. 100(5): p. 1670-8; Ogilvy, S., et al., *Constitutive Bcl-2 expression throughout the hematopoietic compartment affects multiple lineages and enhances progenitor cell survival*. Proc Natl Acad Sci USA, 1999. 96(26): p. 14943-8); however, these commonly used anti-apoptosis treatments are not effective to prevent thrombocytopenia. It has been reported that (1) Bcl-2 and Bcl-xL reduced the production of platelets probably due to the inhibition of microtubule polymerization by Bcl-2 and Bcl-XL (Kaluzhny, Y., et al., *BclxL overexpression in megakayocytes leads to impaired platelet fragmentation*. Blood, 2002. 100(5): p. 1670-8; Ogilvy, S., et al., *Constitutive Bcl-2 expression throughout the hematopoietic compartment affects multiple lineages and enhances progenitor cell survival*. Proc Natl Acad Sci USA, 1999. 96(26): p. 14943-8), and (2) caspase inhibitors markedly decreased platelet formation because caspase activity is required for the release of platelets from megakaryocytes (De Botton, S., et al., *Platelet formation is the consequence of caspase activation within megakaryocytes*. Blood, 2002. 100(4): p. 1310-7). Thus, there is a need for new strategies to protect megakaryocytes from chemotherapy-induced apoptosis without interfering platelet formation activity of megakaryocytes.

BRIEF SUMMARY OF THE INVENTION

The present invention relates to a method of treating chemotherapy-induced thrombocytopenia in a subject. The method can include administering to a subject undergoing chemotherapy a therapeutically effective amount of Bax-inhibiting peptide. The therapeutically effective amount can be an amount effective to mitigate chemotherapy induced apoptosis of megakaryocytes of the subject without substantially inhibiting platelet formation of the megakaryocytes. In one specific embodiment, the peptide can be selected from the group consisting of the VPMLKE (SEQ ID NO:1), VPMLK (SEQ ID NO:2), PMLKE (SEQ ID NO:3), PMLK (SEQ ID NO:4), VPTLK (SEQ ID NO:5), and VPALR (SEQ ID NO:6).

In another embodiment, the peptide is of the following formula: $X^1PX^2LX^3X^4$ (SEQ ID NO: 7), wherein $X^1$ is selected from amino acids with non-polar side chain; $X^2$ is selected from amino acids with non-polar side chain; $X^3$ is selected from amino acids with charged polar side chain; $X^4$ is selected from amino acids with charged polar side chain; and either $X^1$ or $X^4$ may be absent, although both may not be absent.

In one embodiment, the Bax-inhibiting peptide is administered to a patient.

In another embodiment, the invention is a preparation of one of the compositions comprising peptides described above.

The present invention also relates to a method of treating a proliferative disorder in a subject. The method includes administering to the subject a therapeutically effective amount of an anti-proliferative agent and a therapeutically effective amount of a Bax-inhibiting peptide. The proliferative disorder can include cancer and the antiproliferative agent can be administered at an amount effective to treat the cancer. The anti-proliferative agent can be administered at an amount effective to increase the risk of thrombocytopenia in the subject.

In an embodiment of the invention, the therapeutically effective amount of Bax-inhibiting peptide can be an amount effective to mitigate chemotherapy induced apoptosis of megakaryocytes of the subject without substantially inhibiting platelet formation of the megakaryocytes.

In another embodiment of the invention, the peptide can be selected from the group consisting of VPMLKE (SEQ ID NO:1), VPMLK (SEQ ID NO:2), PMLKE (SEQ ID NO:3), PMLK (SEQ ID NO:4), VPTLK (SEQ ID NO:5), and VPALR (SEQ ID NO:6).

In a further embodiment of the invention, the peptide having the following formula: $X^1PX^2LX^3X^4$ (SEQ ID NO: 7), wherein $X^1$ is selected from amino acids with non-polar side chain; $X^2$ is selected from amino acids with non-polar side chain; $X^3$ is selected from amino acids with charged polar side chain; $X^4$ is selected from amino acids with charged polar side chain; and either $X^1$ or $X^4$ may be absent.

DESCRIPTION OF THE INVENTION

Figure 1:
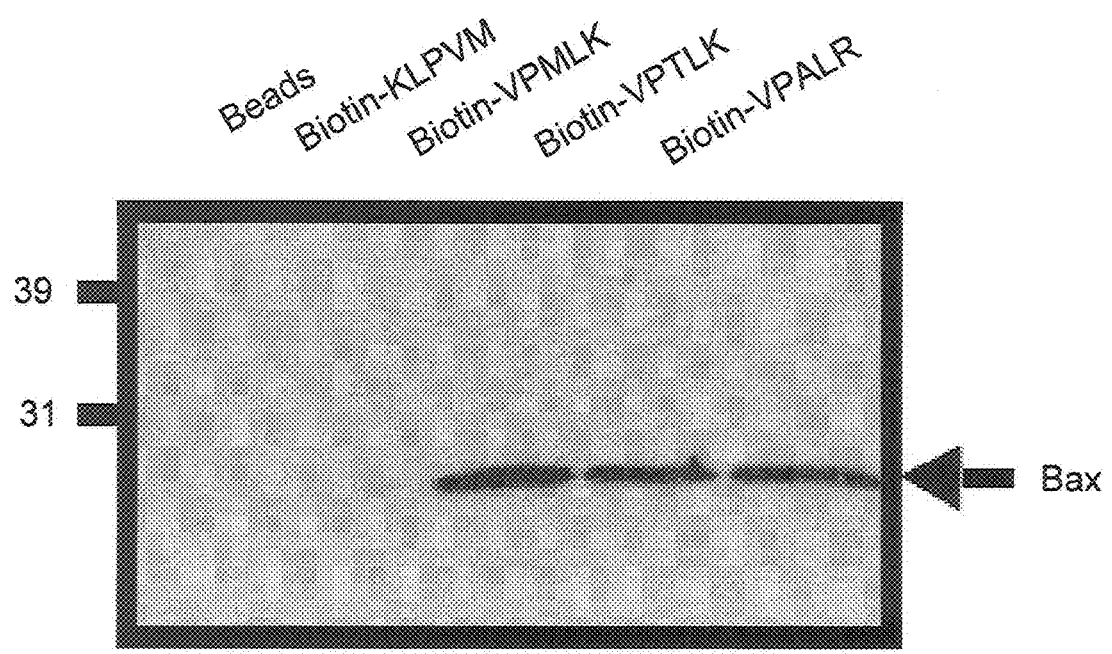
FIG. 1 illustrates Western Blots of Dami cell lysates incubated in the absence or presence of 200 μM biotin-labeled peptides. The peptides were: KLPVM (SEQ ID NO:8) (scrambled negative control), VPMLK (SEQ ID NO:2) (human version), VPTLK (SEQ ID NO:5) (mouse version), and VPALR (SEQ ID NO:6) (rat version). Immuno-precipitation was performed with streptavidin beads. Western blot analysis of immune precipitated samples were performed with anti-Bax polyclonal antibody.

The present invention relates to a method of treating chemotherapy-induced thrombocytopenia in a subject. The method can include administering to a subject undergoing chemotherapy a therapeutically effective amount of Bax-inhibiting peptide (BIP). It was found that BIPs in accordance with the present invention, in contrast to anti-apoptotic proteins, such as Bcl-2, Bcl-XL, and caspase inhibitors, can protect megakaryocytes from chemotherapy induced apoptosis without substantially affecting the ability of megakaryocytes to produce and release platelets. The BIPs in accordance with the invention can therefore be used in combination with antiproliferative agents or chemotherapeutic agents for the treatment of proliferative disorders, such as neoplastic disorders or cancer.

The BIPs in accordance with the invention comprise a membrane permeable peptide (Bax-Inhibiting Peptide; BIP) that inhibits Bax-mediated apoptosis and appears to mimic Ku70 in its interaction with the Bax molecule. In one embodiment, the BIP includes of five amino acids designed from Bax-binding domain of Ku70 and suppresses the mitochondrial translocation of Bax. The BIPs of the present invention can also inhibit Bax-mediated apoptosis induced by saturosporin, UVC irradiation, and anticancer drugs in several types of cells as disclosed below in the Examples.

The Bax-binding domain in Ku70 comprises 6 amino acids (VPMLKE, SEQ ID NO: 1). This peptide (Ku70 Peptide) inhibits the interaction of Ku70 and Bax at the concentration of 20-80 µM in lysates prepared from human cultured cells (HeLa cells and human kidney epithelial 293 cells). Negative control experiments using the scrambled sequence of these 6 amino acids and the immediate next six amino acid sequence of Ku70 (Ku70 573-578 peptide, termed "Ku70 Peptide NC") did not affect the interaction of Ku70 and Bax, indicating the specificity of Ku70 Peptide activity. Delivering the Ku70 peptide into the cells also inhibits mitochondrial translocation of Bax in the cells treated by several apoptotic stresses such, as UV-irradiation and staurosporin-treatment.

Examples of BIPs of the present invention that can be used to treat chemotherapy induced thrombocytopenia, include VPMLKE (SEQ ID NO: 1), VPMLK (SEQ ID NO: 2), PMLKE (SEQ ID NO: 3), PMLK (SEQ ID NO: 4), VPTLK (SEQ ID NO: 5), or VPALR (SEQ ID NO: 6). These peptides suppressed cell death of megakaryocytes treated with the chemotherapeutic, Etoposide, without substantially affecting the ability of the megakaryocytes to produce and release platelets. Advantageously VPMLK (SEQ ID NO:2), PMLKE (SEQ ID NO:3), PMLK (SEQ ID NO:4), VPTLK (SEQ ID NO:5), and VPALR (SEQ ID NO:6) are also cell membrane permeable and do not require a cell delivery system, such as liposomes as in the case of VPMLKE (SEQ ID NO:1).

The original 6 amino acid peptide (VPMLKE; SEQ ID NO:1) and its variants, including shorter amino acid peptides (e.g., VPMLK (SEQ ID NO:2), PMLKE (SEQ ID NO:3), PMLK (SEQ ID NO:4), VPTLK (SEQ ID NO:5), and VPALR (SEQ ID NO:6)) and modified peptides (e.g., modified for better membrane permeablization or longer stability) are also Bax-inhibiting peptides, and may be used to protect cells and tissues from pathological damage in accordance with the present invention.

The present invention also includes peptides (preferably 6-3 residues) and chemicals (natural and synthetic compounds) designed to mimic the described Ku70 peptides. By "mimic," it is meant that the peptide has at least 90% of the Bax-suppressing function of SEQ ID NO:1 or SEQ ID NO:2, as measured by the method of the Examples below. If a peptide or compound suppresses apoptosis by blocking the mitochondrial translocation of Bax, these chemicals or peptides successfully "mimic" Ku70 peptide.

Examples of methods for creating mimics can be found at: WO00/21980, EP1O77218A2, WOO1/60844, WOO1114412, WOO1155091, WOOI/46197, W002/20033, W002/20034, W002/20557, incorporated by reference.

Peptides with slight modifications (e.g., substitution of similar charged amino acids or addition of 1, 2 or 3 innocuous amino acids at either end or by the addition of an innocuous entity or moiety) to the peptide sequences described herein are envisioned to be suitable BIPs. By "innocuous", it is meant that the amino acid(s) or entities do not substantially reduce the Bax-inhibiting activity of the core peptide sequence PMLK (SEQ ID NO: 4). Therefore, a composition comprising a Bax-inhibiting peptide of the present invention includes a peptide described herein (e.g., PMLK (SEQ ID NO: 4), PMLKE (SEQ ID NO: 3), VPMLK (SEQ ID NO: 2), VPMLKE (SEQ ID NO: 1), VPTLK (SEQ ID NO: 5), VPALR (SEQ ID NO: 6) and the formula below) with additions of 1, 2 or 3 innocuous amino acids at either end, innocuous amino acid substitutions, addition of innocuous moieties or entities, and mimics of these peptides.

Peptide drug delivery and therapeutic administration is limited by permeability and selectivity problems involving the cell membrane (Morris, et al., *Nat. Biotechnol.* 19(12): 1173-1176, 2001). Strategies to deliver peptides and proteins into cells may solve these problems. Many small protein domains, called protein transduction domains (PTD's), have been shown to cross biological membranes and act independently from transporters or specific receptors to promote delivery of peptides and proteins into cells. The work of Hawiger (Hawiger, *Curro Opin. Chem. Biol.* 3(1):88-94, 1999) is one example of how this technique involving peptide modification could be applied to create a composition comprising BIP that consists of adding a PTD domain at position $X^1$ or $X^4$ to aid in either the transport of BIP to specific target cells or to aid the stability of the molecule.

The present invention also includes peptides in which sequences described above are repeated multiple times.

Because the amino acid sequences VPMLK (SEQ ID NO:2) and PMLKE (SEQ ID NO:3) are equally effective to suppress Bax, the amino acid sequence PMLK (SEQ ID NO:4) is considered to be the core structure for BIP's biological activity. Indeed, PMLK (SEQ ID NO:4) is sufficient to bind Bax in vitro. However, PMLK (SEQ ID NO:4) is not biologically active because these four amino acids are not retained in the cell. Addition of V before P, or E after K of 40 PMLK (SEQ ID NO:4) causes the peptide(s) to be effectively retained inside the cells. Therefore, these peptides (PMLKE (SEQ ID NO:3)), VPMLK (SEQ ID NO:2), VPTLK (SEQ ID NO:5), VPALR (SEQ ID NO:6)) express anti-Bax activity in cells and are Bax-inhibiting peptides.

The addition of the fifth amino acid to PMLK (SEQ ID NO: 4) is required for either solubility of BIP in the cytosol or protection of the export of BIP through cell membrane. Therefore, other amino acids, which retain similar polarity, are expected to be suitable substitutes for V and E.

In PMLK (SEQ ID NO:4), P and L seem to be required for effectiveness. Because P has very unique structure among amino acids, and substitution of L with I (L and I are non-polar amino acids) diminish BIP's biological activity (described in Nature Cell Biology BIP paper).

In PMLK (SEQ ID NO:4), M and K may be interchangeable with other amino acids in the same group with similar polarity.

Based on the above logic, we describe the formula of the future modification of a preferred embodiment of the BIP as comprising the peptide $X^1PX^2LX^3X^4$ (SEQ ID NO:7), wherein:

$X^1$=Amino acids with non-polar side chain, such as Glycine (G), Alanine (A), Valine (V), Leucine (L), Isoleu-65 cine (1), Methionine (M), Proline (P), Phenylalanine (F), or Tryptophan (W).

$X^2$=Amino acids with non-polar side chain, such as Glycine (G), Alanine (A), Valine (V), Leucine (L), Isoleucine (1), Methionine (M), Proline (P), Phenylalanine (F), Tryptophan (W) or Threonine (T).

$X^3$=Amino acids with charged polar side chain, such as Lysine (K), Arginine (R), Histidine (H), Aspartic acid (D), Glutamic acid (E), and $X^4$=Amino acids with charged polar side chain, such as Lysine (K), Arginine (R), Histidine (H), Aspartic acid (D), Glutamic acid (E).

Either $X^1$ or $X^4$ may be absent.

The BIPs in accordance with the present invention can be administered in a therapeutic amount or therapeutically effective amount to the subject. The term "therapeutic" or "therapeutically" refers to reduction in severity and/or frequency of symptoms, elimination of symptoms and/or underlying cause, prevention of the occurrence of symptoms and/or their underlying cause, and improvement or remediation of disease. For example, treatment of a patient by administration of BIPs of the present invention encompasses reduction in a patient undergoing chemotherapy susceptible to developing thrombocytopenia (e.g., at a higher risk, as a result of genetic predisposition, environmental factors, or the like).

"Effective amounts", in terms of each of the foregoing methods, are amounts of the BIPs effective to mitigate chemotherapy induced apoptosis of megakaryocytes of the subject without substantially inhibiting platelet formation of the megakaryocytes.

The BIPs of the present invention can be provided in the form of pharmaceutical compositions. The pharmaceutical compositions can be administered to any mammal that can experience the beneficial effects of the BIPs of the present invention. Foremost among such animals are humans, although the present invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. The dosage administered will be dependent upon the age, health, and weight of the patient, kind of concurrent treatment, if any, frequency of treatment, and the nature of the effect desired.

In addition to the pharmacologically active compounds, the pharmaceutical preparations of the BIPs can contain suitable pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes.

Formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

In a further aspect of the invention, the BIPs can be used in combination and adjunctive therapies for treating proliferative disorders.

The phrase "combination therapy" embraces the administration of the BIPs and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and cancer. Besides being useful for human treatment, the combination therapy is also useful for veterinary treatment of companion animals, exotic and farm animals, including rodents, horses, dogs, and cats.

In another aspect of the invention, the therapeutic agents administered in combination therapy with the BIPs can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the BIPs consists of antimetabolite-type anti-proliferative agents. Antimetabolites are typically reversible or irreversible enzyme inhibitors, or compounds that otherwise interfere with the replication, translation or transcription of nucleic acids. Such compounds can include, for example, nucleoside analogs. Examples of antimetabolite anti-proliferative agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine (ARA-C), cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, uricytin, and vidarbine all of which are disclosed in U.S. Pat. No. 6,916,800, which is herein incorporated by reference in its entirety.

A second family of anti-proliferative agents, which may be used in combination therapy with the BIPs of the present invention consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, Etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the BIPs of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-11, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the BIPs of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A fifth family of anti-proliferative agents that may be used in combination therapy with the BIPs of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, Etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The BIPs in accordance with the present invention can allow the combination therapeutic agents and therapies of the present invention to be administered at a higher dose, that is, at a dose higher than has been conventionally used in clinical situations because of the risk of thrombocytopenia.

When administered as a combination, the therapeutic agents can be formulated as separate compositions, which are given at the same time or different times, or the therapeutic agents can be given as a single composition.

Alternatively, BIPs of the present invention can be administered in a combination therapy with an agent that stimulates growth of and maturation of megakaryocytes. One example of such an agent is Thrombopoeitin (TPO). TPO known as c-Mpl ligand, is a relatively lineage-specific cytokine that stimulates the growth and maturation of megakaryocytes in vitro (Kuter, D. J. and C. G. Begley, *Recombinant human thrombopoietin: basic biology and evaluation of clinical studies*. Blood, 2002. 100(10): p. 3457-69). Gene-targeting has established that TPO is an important physiologic regulator of steady-state megakaryocyte and platelet production (Carver-Moore, K., et al., *Low levels of erythroid and myeloid progenitors in thrombopoietin-and c-mpl-deficient mice*. Blood, 1996. 88(3): p. 803-8; Gainsford, T., et al., *Cytokine production and function in c-mpl-deficient mice: no physiologic role for interleukin-3 in residual megakaryocyte and platelet production*, Blood, 1998. 91(8): p. 2745-52; Gainsford, T., et al., *The residual megakaryocyte and platelet production in c-mpl-deficient mice is not dependent on the actions of interleukin-6, interleukin-11, or leukemia inhibitory factor*. Blood, 2000. 95(2): p. 528-34). Based on these observations, TPO is now being used to reduce the thrombocytopenia caused by chemotherapy (Kuter, D. J. and C. G. Begley, *Recombinant human thrombopoietin: basic biology and evaluation of clinical studies*. Blood, 2002. 100(10): p. 3457-69; Carver-Moore, K., et al., *Low levels of erythroid and*

*myeloid progenitors in thrombopoietin-and c-mpl-deficient mice.* Blood, 1996. 88(3): p. 803-8; Mughal, T. I., *Current and future use of hematopoietic growth factors in cancer medicine.* Hematol Oncol, 2004. 22(3): p. 121-34; Parvez, T., et al., *Scope of growth factor in cancer patients.* J Coll Physicians Surg Pak, 2005. 15(6): p. 375-7). If TPO is administrated together with BIP, the chemotherapy-induced thrombocytopenia may be inhibited more efficiently than single treatment of TPO.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

The present Example shows that BIPs effectively suppressed chemotherapy-induced apoptosis in megakaryocytic cell line (Dami cells) (Greenberg, S. M., et al., *Characterization of a new megakaryocytic cell line: the Dami cell.* Blood, 1988. 72(6): p. 1968-77) and primary cultured mouse megakaryocytes. Importantly, BIP did not interfere the production of platelet-like particles in primary cultured mouse megakaryocytes. The results show that BIPs and their derivatives may be useful for the protection of megakaryocytes to relieve chemotherapy-induced thrombocytopenia involving chemotherapy-induced apoptosis in megakaryocytes.

Materials and Methods
Peptide Synthesis and Preparation.

The synthesis and preparation of peptides were performed as described previously (Yoshida, T., et al., *Bax-inhibiting peptide derived from mouse and rat Ku70.* Biochem Biophys Res Commun, 2004. 321(4): p. 961-6). Briefly, peptides were synthesized using the standard 9-fluorenylmethoxycarbonyl (FMOC) protocol on an ABI 433 (Applied Biosystems). Amino acids were activated using 2-(1H-benzotriazol-1-yl)-1,1,3,3-tetramethyluronium hexafluorophosphate (HBTU) in dimethylformamide (DMF) and deblocked using 25% piperidine in N-methylpyrrolidone (NMP). The resin was rinsed with dichloromethane (DCM) and lyophilized overnight. Peptides were cleaved from the resin using 95% trifluoracetic acid (TFA), and 2.5% triisopropylsilane (TIS), 2.5% $H_2O$. The precipitate was washed three times in ethyl ether, dissolved in 5% acetic acid, and lyophilized. Peptides were purified by reverse-phase HPLC using a Vydac 218TP1022 column (1% TFA in acetonitrile) on a Beckman HPLC system. Peptide mass was verified using matrix assisted laser desorption/ionization time of flight mass spectrometry (MALDI-TOF), performed at the Protein/Nucleic Acid Core Facility of the Medical College of Wisconsin (Milwaukee, Wis.). Dried peptide powders were stored at −30° C. The peptides were dissolved in fresh dimethyl sulfoxide (DMSO; Sigma) at 200 mM in plastic tubes (Coaster), and 5 μl of each solution was dispensed to individual 0.5-ml plastic tubes (Coaster). These 5-μl aliquots were used as stocks. All tubes were stored at −20° C., and each tube was used only one time to minimize freeze-thaw degradation.

Cell Culture

Human embryonic kidney (HEK) 293T cells were cultured in Dulbecco's modified eagle's medium (DMEM) supplemented with 10% fetal bovine serum (FBS) and 1% penicillin and streptomycin. Dami cells were cultured in Iscove's Modified Dulbecco's medium (IMDM: Gibco) supplemented with 10% horse serum and 1% penicillin and streptomycin. For the cell culture of mouse megakaryocytes, anesthetized C57BL/6 mice of 8-10 weeks of age (20 mice for one experiment) were killed and bone marrow flushed from the femurs and tibias into IMDM supplemented with 1% penicillin, streptomycin, and glutamine. Mononuclear cells were suspended in culture by vigorous mixing using a syringe and 18-G needle. The mononuclear cells were then purified with ficoll (Atlanta biologicals). Bone marrow cells were cultured in megakaryocytic selective medium at a cell density of $2\times10^6$ cell/ml and incubated at 37° C. with 5% $CO_2$. Bone marrow was obtained from C57BL/6 mice and cultured in megakaryocytic selective medium, consisting of: IMDM, 2% deionized bovine serum albumin (BSA), 10 μM β-mercaptoethanol (BME), 1% penicillin, streptomycin, and glutamine, 200 μg/ml holo-bovine-transferrin (Sigma), 10 μg/ml bovine-zinc-insulin (Sigma), 1% lipid concentrate (Gibco), 10% knock-out serum (Gibco), 10 ng/ml murine thrombopoietin (TPO) (Peprotech), 10 ng/ml murine IL-6 (Peprotech), and 10 ng/ml human IL-11 (Peprotech). On the 7th day, the large megakaryocytes were harvested using a gradient of deionized BSA (1-3%). These megakaryocytes were ready to be used in the BIP treatment experiment. All mice were housed in the Medical College of Wisconsin's Animal Resource Center, a facility approved by the American Association for the Accreditation of laboratory Animal Care (Johnson, B. D., et al., *Role of immunoregulatory donor T cells in suppression of graft-versus-host disease following donor leukocyte infusion therapy.* J Immunol, 1999. 163(12): p. 6479-87).

Analysis of the Binding of Peptides to Bax.

Co-precipitation was performed as previously described (Yoshida, T., et al., *Bax-inhibiting peptide derived from mouse and rat Ku70.* Biochem Biophys Res Commun, 2004. 321(4): p. 961-6). Dami cells (approximately $3\times10^8$ cells) were lysed in 1.5 ml of Chaps buffer (150 mM NaCl, 10 mM Hepes at pH 7.4 and 1.0% Chaps) containing protease inhibitors (Protease Inhibitor Cocktail, Sigma, diluted 1:100) and 1 mM phenylmethylsulfonyl fluoride (PMSF). The cell lysate was prepared by collecting the supernatant after centrifugation (14000 rpm) at 4° C. for 30 min. The protein concentration of the cell lysate was adjusted to 7.5 mg/ml. After the precleaning of 200 μl of sample with 20 μl of streptavidin beads (Amersham-Pharmacia Biotech) at 4° C. for 1 h, the samples were incubated with 200 μM of various biotin-labeled peptides (biotin-KLPVM (SEQ ID NO:8), VPMLK (SEQ ID NO:2), VPTLK (SEQ ID NO:5) or VPALR (SEQ ID NO:6) for 2 h. Streptavidin beads (20 μl) were added to the samples and the mixtures were incubated at 4° C. After 2 h of incubation, the beads were washed with 100 μl of Chaps buffer 3 times by centrifugation (1000 rpm, at 4° C., 15 sec). The beads were boiled in 40 μl of Laemmli buffer and the eluted proteins (20 μl) were analyzed by Western blotting with anti-human Bax polyclonal antibody (BD-Pharmingen).

Analysis of Cell Penetrating Activity of BIPs

For the examination of the cell penetrating activity of Fluorescein (Flu) labeled peptides (Flu-VPMLK (SEQ ID NO:2), VPTLK (SEQ ID NO:5), VPALR (SEQ ID NO:6), and KLPVM (SEQ ID NO:8), Dami cells (5.0×10⁴/ml) and primary mouse megakaryocytes (1.0×10⁴/ml) were incubated with 200 μM of Flu-labeled peptides for 1, 6, 24 or 48 h. The cells were analyzed under a fluorescence microscope (Nikon; TE200) and a confocal scanning laser microscope (Leica; TCS SP2 to detect fluorescence dye inside the cells) to detect fluorescein labeled peptides in the cell.

Detection of Apoptosis (HEK293T Cells, Dami Cells, and Primary Cultured Mouse Megakaryocytes).

To confirm whether mouse and rat versions of BIP (VPTLK (SEQ ID NO:5) and VPALR (SEQ ID NO:6)) protect Bax-induced cell death in HEK293T cells, Bax was over expressed by transfection of pcDNA3-Bax (1 μg of pcDNA3-human Bax for 1.0×10⁵ HEK293T cells/3 ml, 6-cm diameter dish) in the presence of BIPs (VPTLK (SEQ ID NO:5) and VPALR (SEQ ID NO:6)) and their negative control peptide (KLPVM (SEQ ID NO:8)). Transfections of plasmids were performed with Superfect (Qiagen, Valencia, Calif.) in accordance with the manufacturer's instructions. BIPs were added to the culture media 1 hr before the transfection, and then were added to the fresh medium after the 3 h of incubation with the lipid DNA complexes.

To determine the effects of BIPs on Dami cells, cells (5.0×10⁴ cells/ml, 24 wells) were pre-incubated with various concentrations of the peptides (50-400 μM: KLPVM (SEQ ID NO:8), VPMLK (SEQ ID NO:2), VPTLK (SEQ ID NO:5), and VPALR (SEQ ID NO:6)) for 24 h. After the pre-incubation, 1 or 5 μM Etoposide was added to the culture medium for 24 hrs. Dami cells (1.0×10⁴, cells/ml, 24 wells) were also pre-incubated with 400 μM of BIPs for 24 h, after which 5 μM cisplatin, 1 μM paclitaxel, or 0.25 μM doxorubicin were added for 24 hrs to examine the effects of BIPs on apoptosis induced by these drugs.

To determine the effects of BIPs on primary cultured mouse megakaryocytes, cells (1.0×10⁴/ml, 24 wells) were pre-incubated with 200 μM of the peptides (KLPVM (SEQ ID NO:8, VPMLK (SEQ ID NO:2), VPTLK (SEQ ID NO:5), and VPALR (SEQ ID NO:6)) for 48 h, and Etoposide (1 or 5 μM) was added to the culture medium for 24 hrs.

To detect cells undergoing apoptosis, the cells were stained with Hoechst dye and apoptotic nuclei were counted under a fluorescence microscope (Nikon: TE200) (two hundred cells were counted for each experiment with HEK293T cells and Dami cells, and three hundred for experiments with primary cultured mouse megakaryocytes), as previously reported (Yoshida, T., et al., *Bax-inhibiting peptide derived from mouse and rat Ku70*. Biochem Biophys Res Commun, 2004. 321(4): p. 961-6). Each point in the figures showing percent apoptosis represents the mean±SEM of three experiments.

Analysis of Platelet Formation In Vitro

The cultured mouse megakaryocytes were incubated with VPTLK (200 μM) (SEQ ID NO:5), and caspase inhibitor (Z-VAD-fmk; 200 and 400 μM) for 48 h. After the pre-incubation with the peptides, 1 mM EDTA and 50 ng/ml prostaglandin E₁ (Sigma) dissolved in ethanol were added to the cell culture before the centrifugation (700 g) at room temperature (RT) for 10 min. The platelets were washed with 300 μl of tyrodes buffer (pH 7.4) containing 2.5 mg/ml BSA and 1 mg/ml glucose. Then 2 μl of anti CD16/anti CD32 (BD Phaminogen™) was added to the platelets. The platelets were incubated at RT for 10 min. The platelets were divided into 3 sets, and 2 μl of rat IgG₁ κ phycoerythrin (PE) labeled isotype control (Pharmingen) was added to one sample, and 2 μl of PE labeled antibody of intregin αIIB PE (Santa Cruz) was added to the other two samples. The platelets were incubated at RT for 30 min. Finally, 5 μl of Flow-Count™ Fluorospheres (Beackman-Coulter™) was added to the sample as platelet size marker. The platelets were detected with a FACScan flow cytometer system (Becton Dickinson; BD LSRII) using cellquest software. Each point in the figures showing percent apoptosis represents the mean±SEM of three experiments.

Analysis of Platelet Number in Mouse Peripheral Blood.

Mouse blood (50-100 micro 1) was collected by heparin-coated capillary tube from tail, and the samples were incubated at room temperature for 1 hr before blood cell analysis using HEMA VET blood cell counter (Drew Scientific Inc. Oxford, Conn.). Each blood sample was measured twice, and the mean value of two measurements was used as one sample data (n=1).

BIPs Suppress Bax-Mediated Cell Death in HEK293T Cells and Bind Bax in Dami Cells.

In this example, a human pro-megakaryocyte cell line (Dami cell) was used to examine the ability of BIPs to inhibit chemotherapy-induced cell death. To confirm the Bax-binding activity of these peptides in Dami cells, biotin-labeled peptides were added to cell lysates and the peptides were precipitated using streptavidin beads as reported previously (Yoshida, T., et al., *Bax-inhibiting peptide derived from mouse and rat Ku70*. Biochem Biophys Res Commun, 2004. 321(4): p. 961-6). As shown in FIG. 1, Bax was pulled down by BIPs but not by a scrambled negative control peptide (KLPVM (SEQ ID NO:8)), suggesting that Bax binds equally to these peptides derived from human, mouse, and rat Ku70 in Dami cells.

BIP Entered Dami Cells and Primary Cultured Mouse Megakaryocytes.

Figure 2:
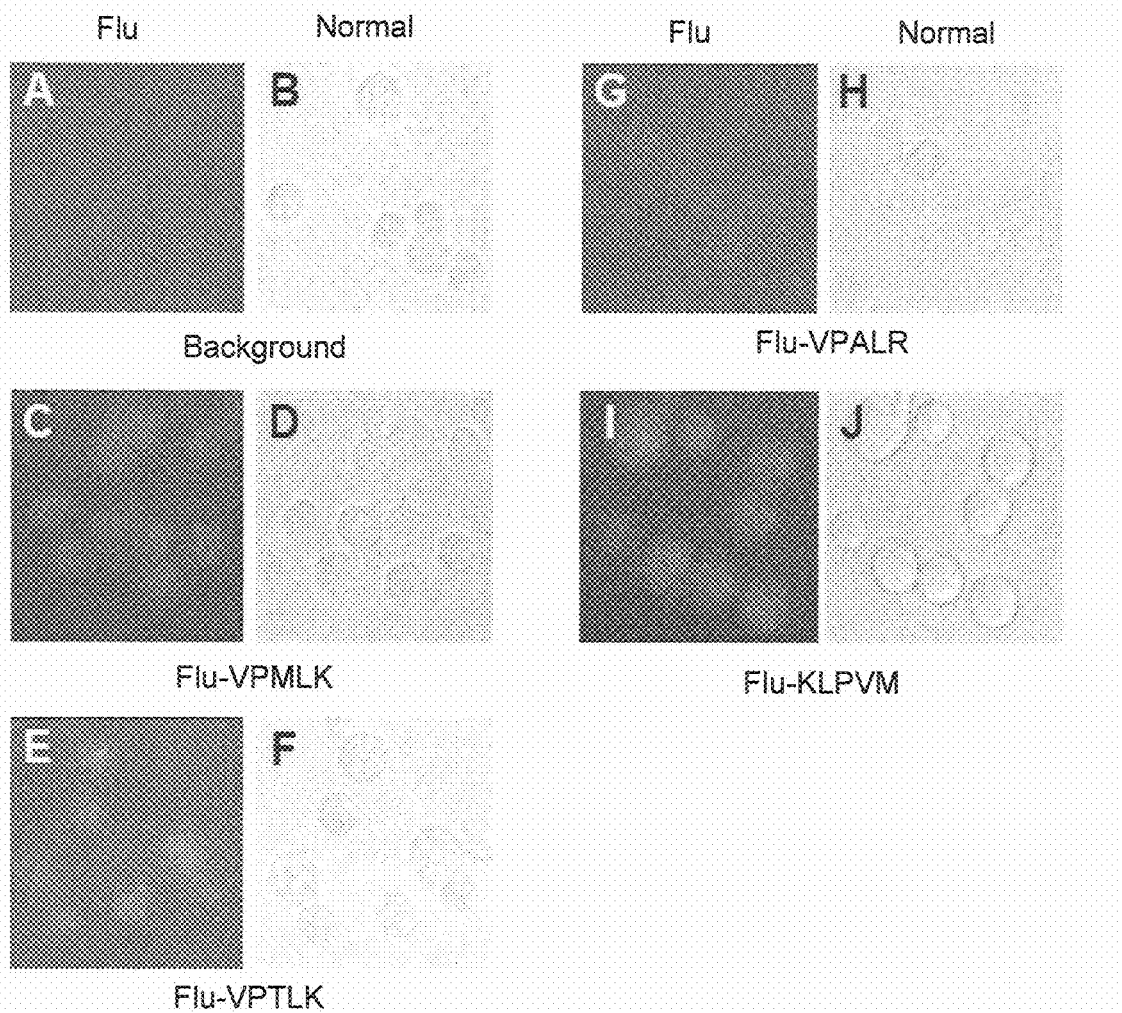
FIG. 2 illustrates fluorescence microscopic analysis of Dami cells incubated with Fluorescein-labeled BIPs (Flu-BIPs) and their negative control peptide (KLPVM) (SEQ ID NO:8). (A-J) Dami cells were incubated with 200 μM Flu-labeled peptides for 24 h before being analyzed by fluorescence microscopy. (A, B) No peptide (background fluorescence), (C, D) Flu-VPMLK. (E, F) Flu-VPTLK (SEQ ID NO:5). (G, H) Flu-VPALR (SEQ ID NO:6). (I, J) Flu-KLPVM (SEQ ID NO:8). A, C, E, G and I show normal fluorescence micrographs. B, D, F, H, and J show phase contrast normal micrographs. All micrographs are 40× magnification.
Figure 3:
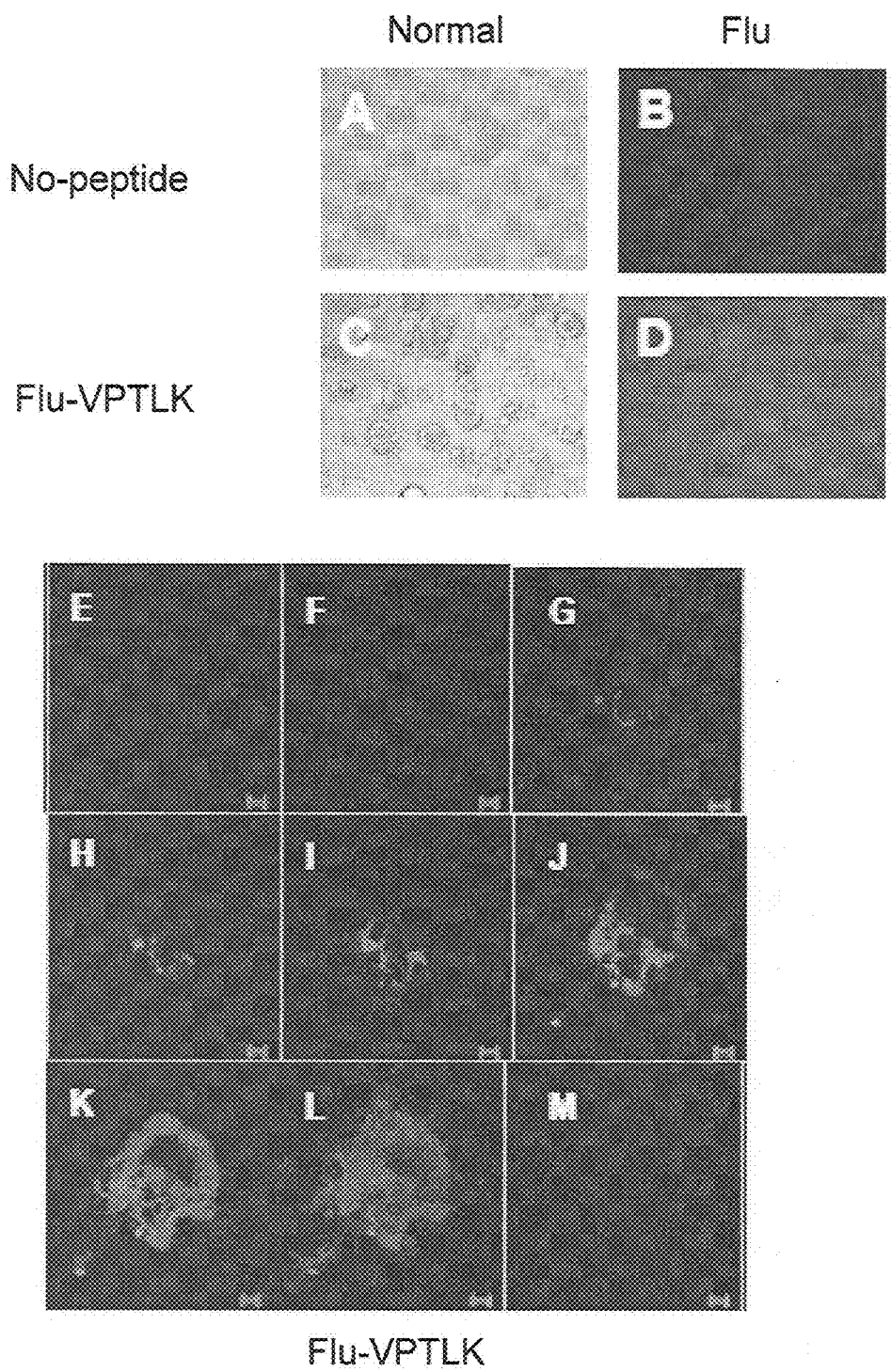
FIG. 3 illustrates a microscopic analysis of primary cultured mouse megakaryocytes incubated with Flu-VPTLK (SEQ ID NO:5). (A-M) Primary cultured mouse megakaryocytes were incubated with 200 μM Flu-VPTLK (SEQ ID NO:5) for 48 h before being analyzed by microscope. Normal microscope analysis.(A-D). (A and B) no peptide (background fluorescence). (C and D) Flu-VPTLK (SEQ ID NO:5). A and C phase contrast micrographs. All micrographs are 40× magnification. Confocal microscope analysis (E-M). (E-M) slice images (X-Y planes) confirming the presence of Flu-VPTLK (SEQ ID NO:5) in the cell. Bar corresponds to 10 μm. The magnification is 63×.
Figure 4A:
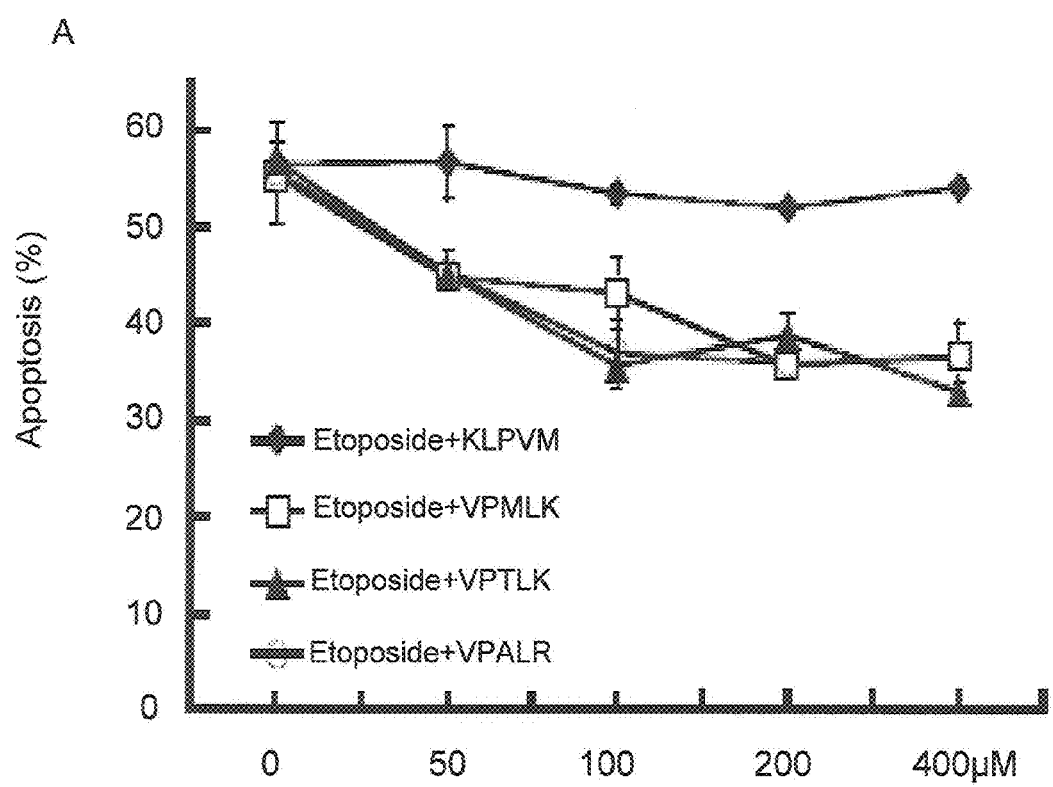
FIG. 4 illustrates that BIPs inhibit drug-induced apoptosis in Dami cells. (A) Cells were pre-incubated for 24 h with different concentrations of VPTLK (SEQ ID NO:5), VPMLK (SEQ ID NO:2), VPALR (SEQ ID NO:6), and KLPVM (SEQ ID NO:8) before Etoposide treatment. Cells were further incubated with Etoposide (5 μM) for 24 h in the presence of peptides, and the percentage of apoptosis was determined using Hoechst dye nuclear staining. (B-E) cells were pre-incubated with the peptides (400 μM) for 24 h before the addition of the drug indicated. Cells were incubated further for 24 h in the presence of drugs indicated and peptides. The percentage of apoptosis was determined by Hoechst dye nuclear staining.
Figure 4B:
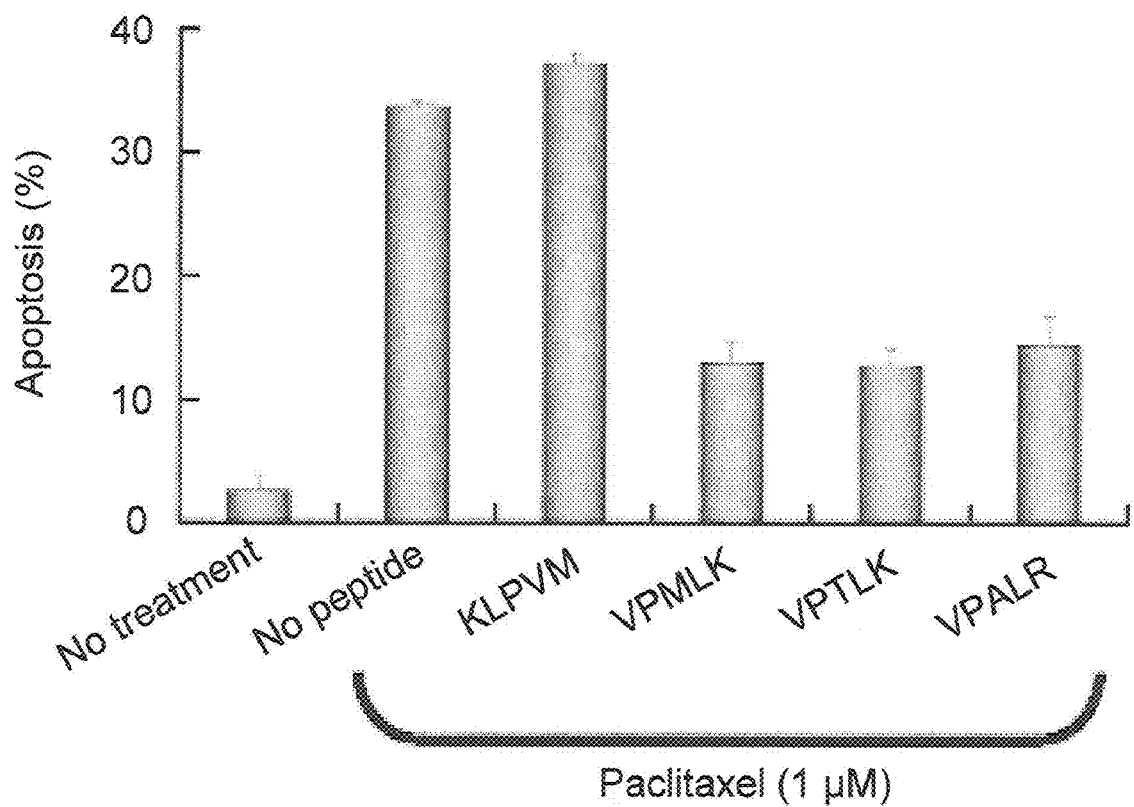
Figure 4C:
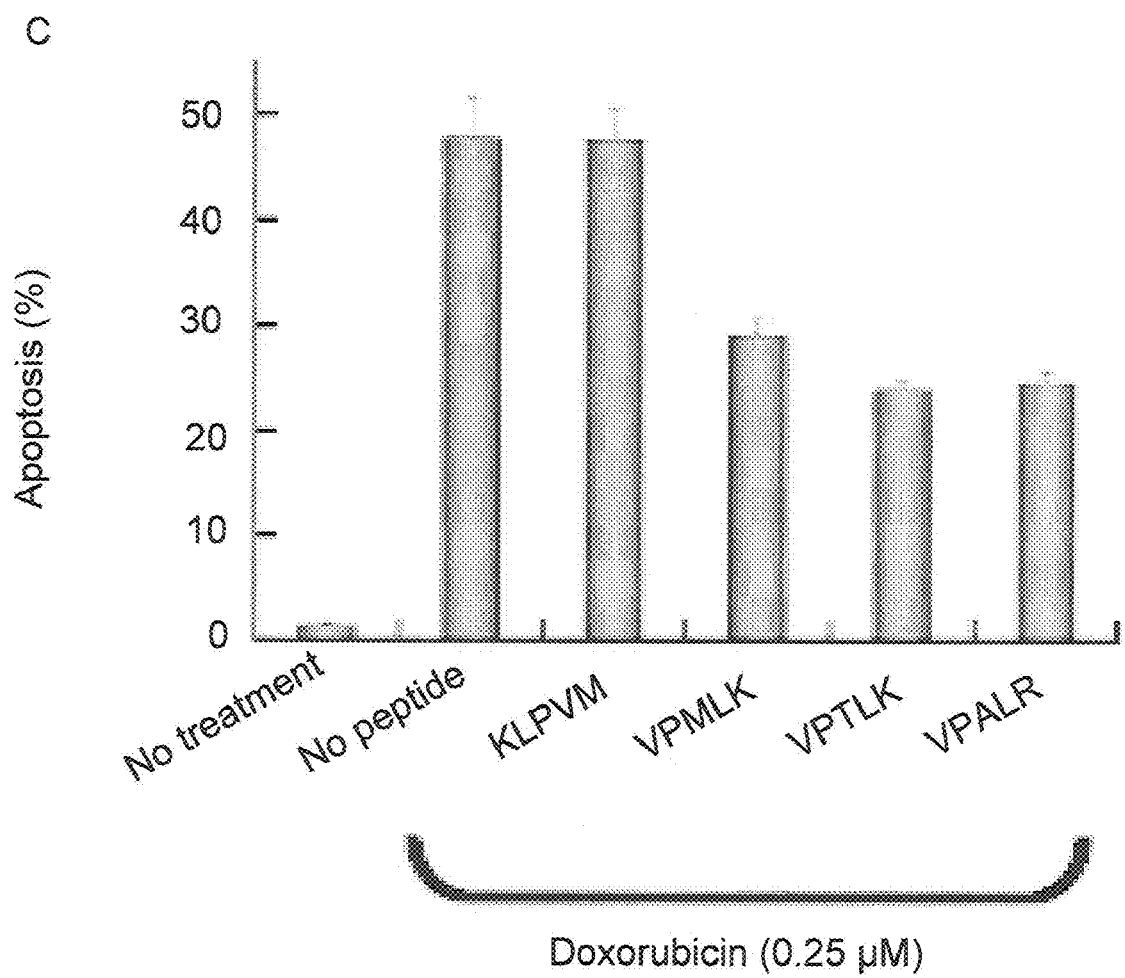
Figure 4D:
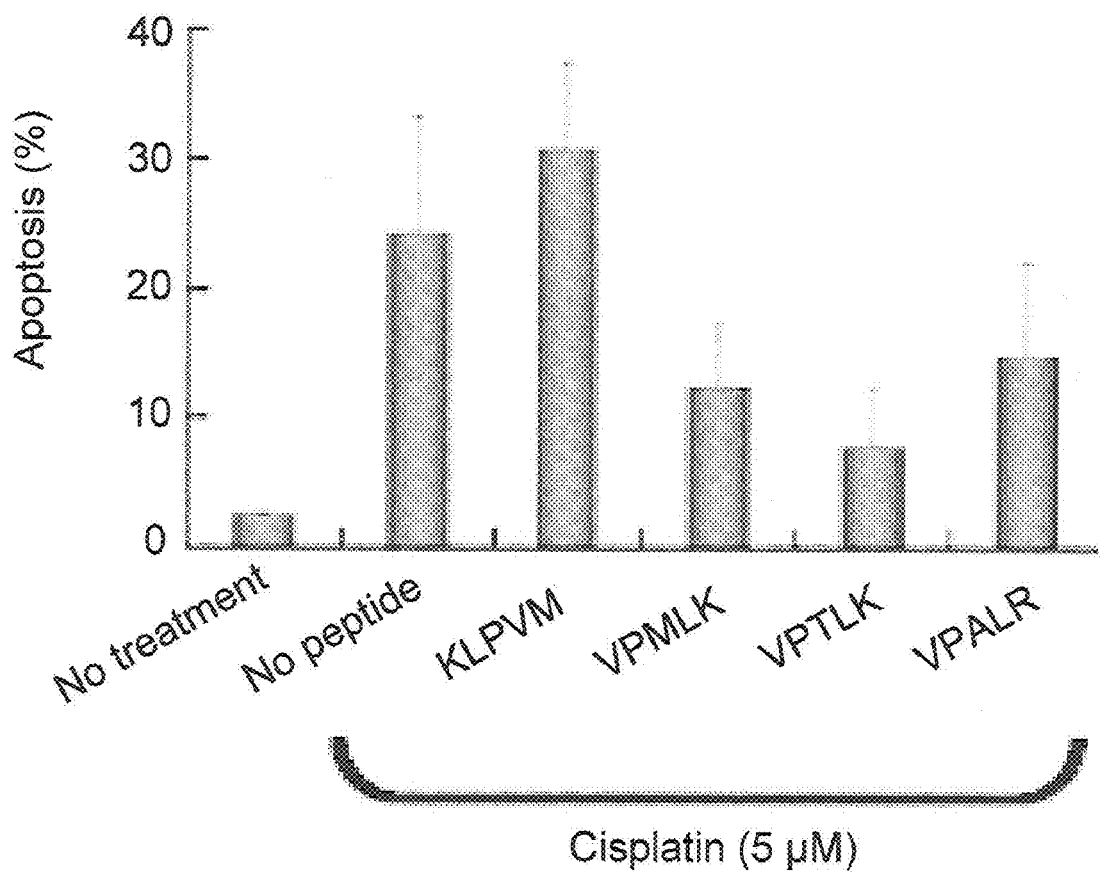
Figure 4E:
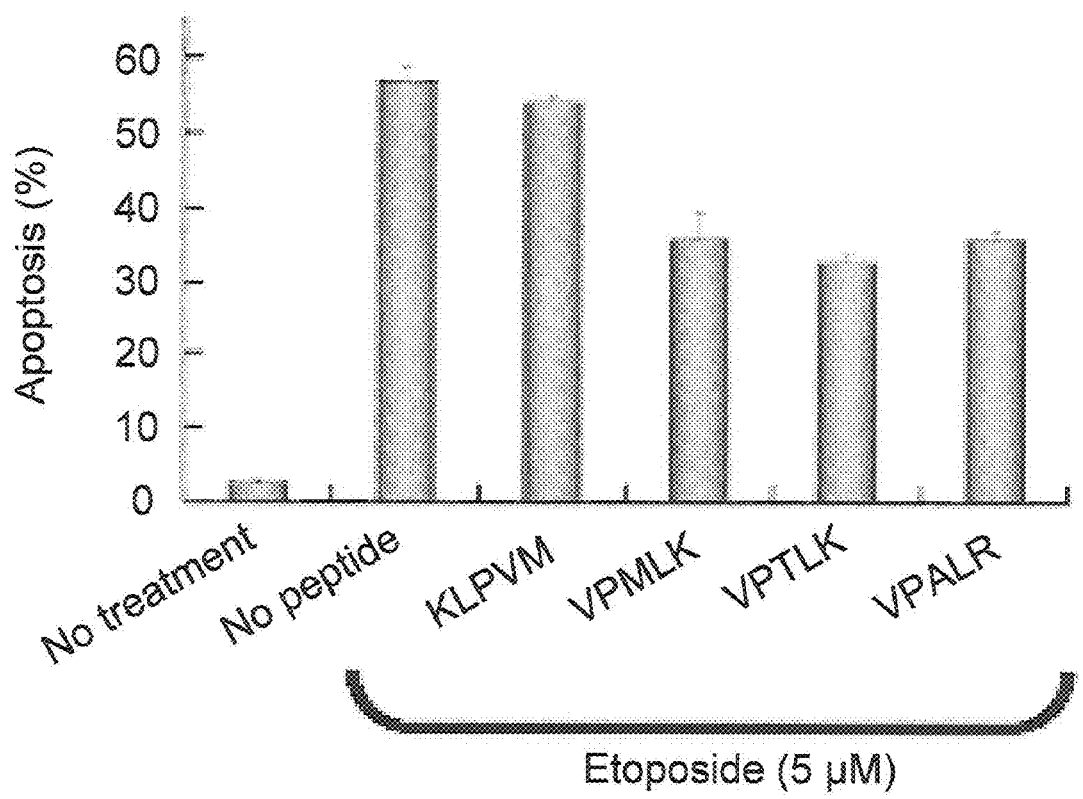

We previously reported that human, mouse, and rat Ku70 peptides were able to enter the cytosol of a mouse myeloid cell line (32D (EpoR wt)) and cumulus cells of three species (mouse, rat, and porcine) (Yoshida, T., et al., *Bax-inhibiting peptide derived from mouse and rat Ku70*. Biochem Biophys Res Commun, 2004. 321(4): p. 961-6). BIPs and KLPVM (SEQ ID NO:8) (scrambled negative control) were N-terminally labeled with Fluorescein (Flu) and then used to check cell permeability in Dami cells. Cell permeability was examined by incubating cells with Flu-labeled BIPs, and detecting Fluorescein by fluorescence and confocal scanning laser microscope. All BIPs entered Dami cells (FIG. 2). FIGS. 2A-H showed fluorescence microscopic images of Dami cells cultured for 24 h in the presence of the Flu-labeled peptides. The incorporation of the peptides was detected at 15 minutes after the incubation, and reached a maximum at 6 h (data not shown). VPTLK showed the best cell permeability among all BIPs tested (FIGS. 2A-H). VPTLK (SEQ ID NO:5) showed cell permeability in primary cultured mouse megakaryocytes, too (FIG. 3). FIG. 3 shows fluorescence microscopic and confocal microscopic images of primary cultured mouse megakaryocytes cultured for 48 h in the presence of Flu-labeled VPTLK (SEQ ID NO:5). In the case of primary cultured mouse megakaryocytes, an incubation period of 48 h was required to observe significant incorporation of Flu-BIP in the cell.

BIP Protects Dami Cells and Primary Cultured Mouse Megakaryocytes from Apoptosis Induced by Anti-Cancer Drugs.

Figure 5A:
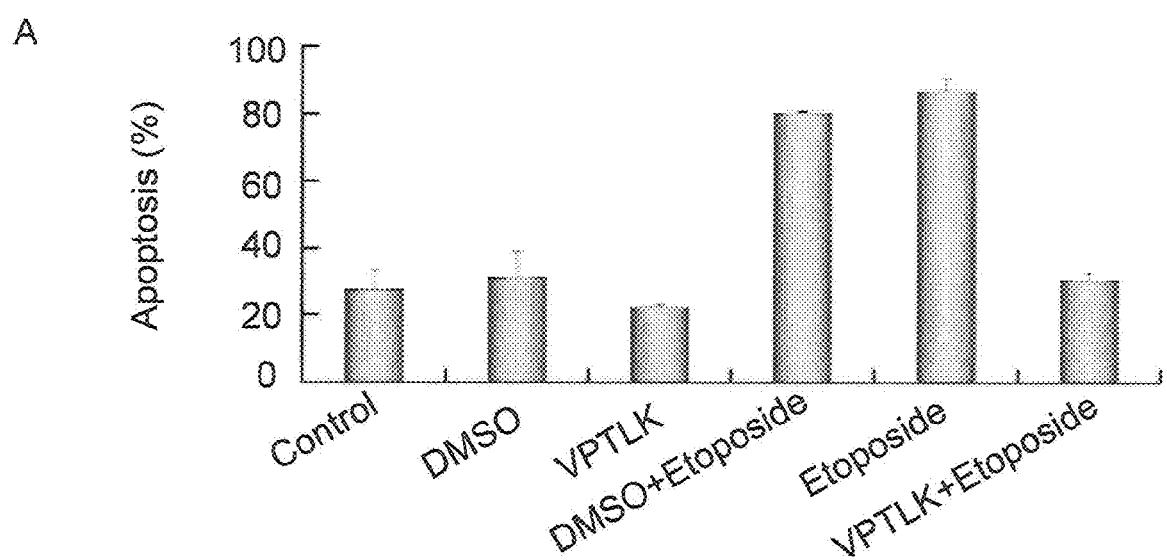
FIG. 5 illustrates VPTLK (SEQ ID NO:5) inhibits Etoposide-induced apoptosis in primary cultured mouse megakaryocytes without interfering platelets formation activity. (A) Primary cultured mouse megakaryocytes were pre-incubated with 200 μM VPTLK (SEQ ID NO:5) for 48 h before being treated with Etoposide. One day (24 h) after the Etoposide treatment, apoptotic cells were counted as described in materials and methods. (B) Megakaryocytes were incubated with VPTLK (SEQ ID NO:5) (200 μM) or a caspase inhibitor (Z-VAD-fmk; 200 and 400 μM) for 48 h. After the culture, platelet like small particles were collected, and they were incubated with anti CD16 and anti CD32 at RT for 10 min. Then, the particles were incubated with Phycoerythrin (PE) labeled rat $IgG_1$ (κ isotype control) or anti-intregin αIIB PE-labeled at RT for 30 min. Finally, 5 μl of Flow-Count™ Fluorospheres (artificial particle with the size of platelet) was added to the sample to detect particles with the size of platelets by FACS. Y-axis of the graphs shows the number of particles with integrin αIIB expression that have similar size of platelet.

Bax is widely expressed in human cells including megakaryocytes and platelets (Vanags, D. M., S. Orrenius, and M. Aguilar-Santelises, *Alterations in Bcl-2/Bax protein levels in platelets form part of an ionomycin-induced process that resembles apoptosis*. Br J Haematol, 1997. 99(4): p. 824-31; Doherty, A. J. and S. P. Jackson, *DNA repair: how Ku makes ends meet*. Curr Biol, 2001. 11(22): p. R920-4), suggesting that BIP may be utilized to protect megakaryocytes from the side effects of chemotherapy. We examined the influence of BIPs on chemotherapy-induced apoptosis in Dami cells and primary cultured mouse megakaryocytes. Apoptosis was induced in Dami cells by treatment with Etoposide, cisplatin, paclitaxel, and doxorubicin, all commonly used anti-cancer drugs. Paclitaxel, doxorubicin, cisplatin, or Etoposide-induced apoptosis of Dami cells was suppressed at 400 μM of BIPs (FIG. 4). We also tested the effects of BIP, VPTLK (SEQ ID NO:5), on Etoposide-induced apoptosis in primary cultured mouse megakaryocytes, and confirmed that VPTLK (SEQ ID NO:5) significantly blocked apoptosis in this cell type (FIG. 5A).

BIP (VPTLK) does not Interfere with Platelet Formation in Primary Cultured Mouse Megakaryocytes.

Figure 5B:
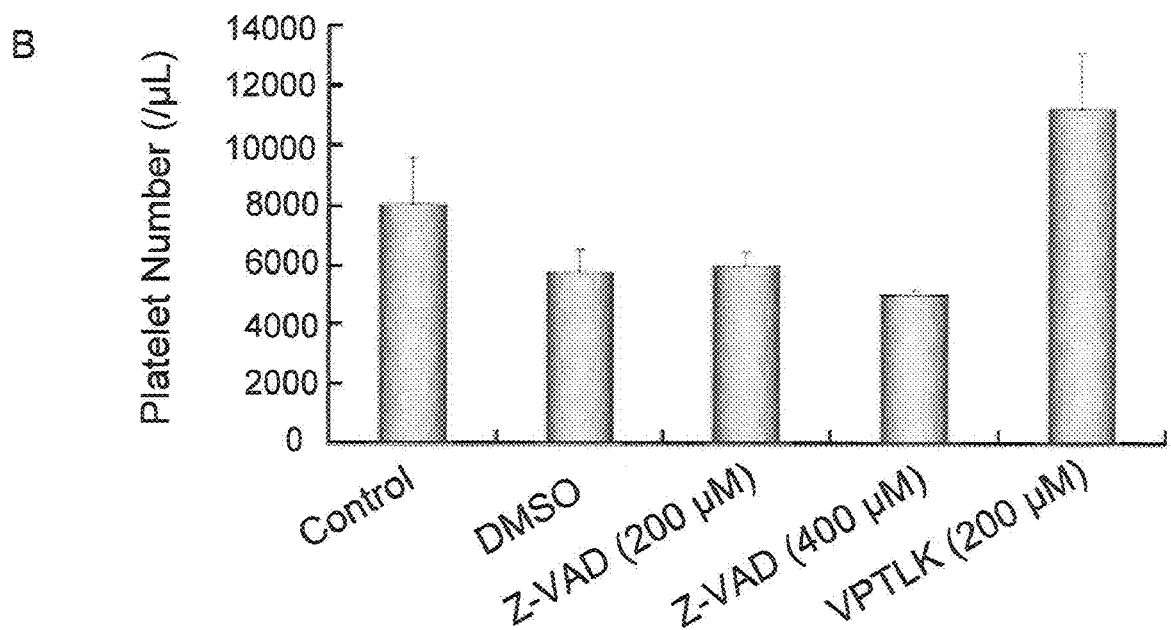

Caspase inhibitors are used for the protection of several cell types from drug-induced apoptosis in laboratory research (Slee, E. A., et al., *Benzyloxycarbonyl-Val-Ala-Asp (OMe) fluoromethylketone (Z-VAD.FMK) inhibits apoptosis by blocking the processing of CPP*32. Biochem J, 1996. 315 (Pt 1): p. 21-4). However, it has been reported that caspase inhibitors markedly decrease platelet formation because caspase activity is required for platelet cleavage from megakaryocytes (De Botton, S., et al., *Platelet formation is the consequence of caspase activation within megakayocytes*. Blood, 2002. 100 (4): p. 1310-7; Clarke, M. C., et al., *Compartmentalized megakayocyte death generates functional platelets committed to caspase-independent death*. J Cell Biol, 2003. 160(4): p. 577-87). Since the caspase inhibitor itself suppresses platelet formation (De Botton, S., et al., *Platelet formation is the consequence of caspase activation within megakaryocytes*. Blood, 2002. 100(4): p. 1310-7), this apoptosis inhibitor cannot be used to reduce thrombocytopenia. Here, we examined the effect of BIP and caspase inhibitor on in-vitro pro-platelet formation activity of mouse megakaryocytes. The cultured primary mouse megakaryocytes develop normally under selection media and they go onto pro-platelets after 8 to 11 days in culture (Choi, E. S., et al., *Platelets generated in vitro from proplatelet-displaying human megakayocytes are functional*. Blood, 1995. 85(2): p. 402-13). This culture produces Integrin αIIB positive platelets like particles starting at day 9 from mature large mouse megakaryocytes. To examine the effect of inhibitors of Bax (BIP) and caspase, the inhibitors were added to harvested large mouse megakaryocytes cultured in megakaryocytes selective media. The large mouse megakaryocytes were harvested at day 7 after selection from mouse bone marrow. On day 9, the production of platelets like particles was detected by flow cytometry identified by detecting Integrin αIIB positive particles. Consistent with a previous report (De Botton, S., et al., *Platelet formation is the consequence of caspase activation within megakaryocytes*. Blood, 2002. 100(4): p. 1310-7), Z-VAD-fmk treatment slightly decreased platelet like particles formation. However, the solvent (DMSO) of Z-VAD-fmk and BIP also showed slight suppression (FIG. 5B). Therefore, the suppression of platelet like particles formation activity by caspase inhibitor was not clearly confirmed in this experiment. Importantly, BIP treatment did not inhibit platelet like particles formation activity of cultured megakaryocytes, and it actually slightly enhanced it (FIG. 5B). This slight enhancement is probably due to the protection of megakaryocytes from autonomous cell death in culture rather than a promotion of platelet like particles production by each megakaryocyte.

BIP Treatment Blocked Etoposide-Induced Platelet Number Decrease in Mouse.

Figure 6:
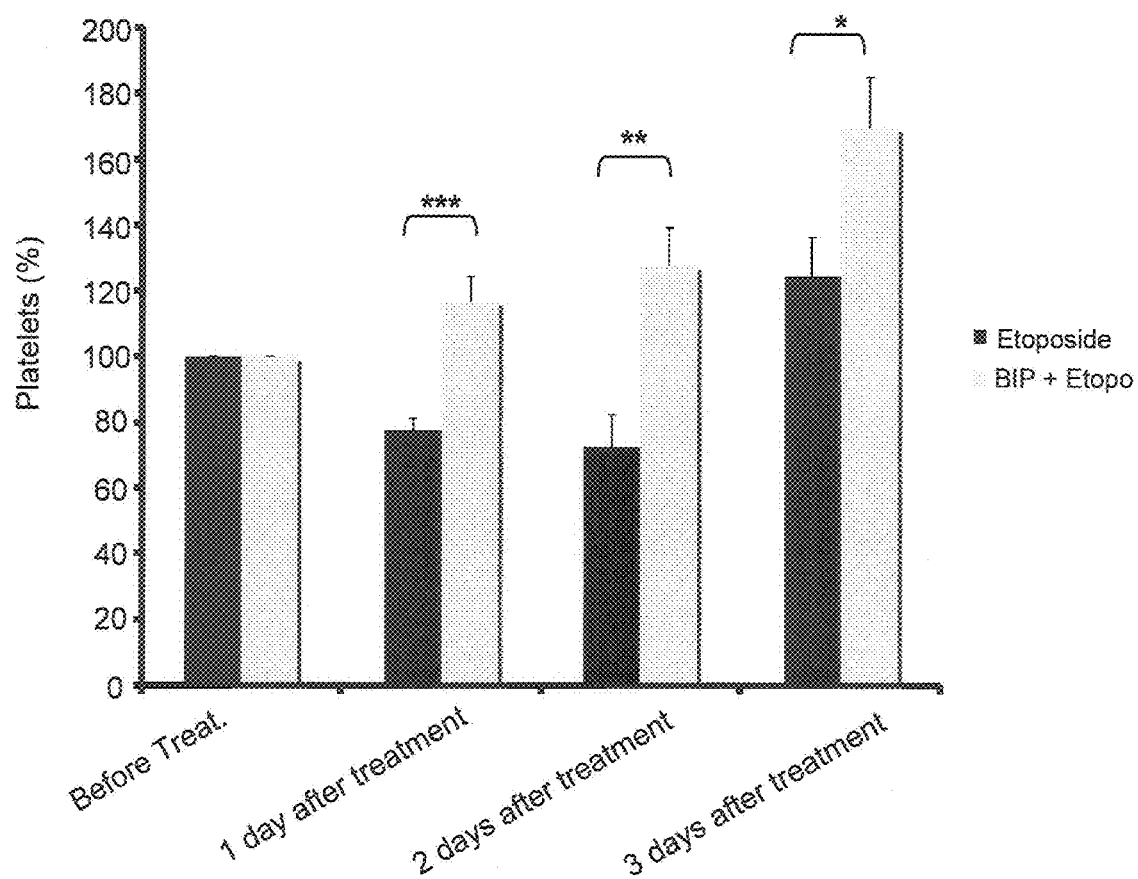
FIG. 6 illustrates Mouse Bax Inhibiting Peptide (VPTLK (SEQ ID NO:5)) inhibited Etoposide induced platelets decreased in C57/B6 mice. Percentage of platelets in C57BL/6J mice compared to before treatment (100%). Animals were pretreated with mouse BIP (VPTLK-166 mg/kg) (SEQ ID NO:5) and 30 min later treated with Etoposide (150 mg/kg), in total 10 mice (male and female) were treated, another group of animals was treated with Etoposide (150 mg/kg), in total 9 mice (male and female) were treated. The statistical significance was determine by an unpaired student t test, *P<0.05, P<0.01, *, P<0.001.

Etoposide (150 mg/kg, i.p.) treatment induced a slight decrease of platelet count in the peripheral blood for 48 hrs (FIG. 6). Pretreatment of mice with BIP (166 mg/kg, i.p.) significantly suppressed this effect of Etoposide, and BIP-treated mice showed higher platelet number than non-treated mice for 3 days after Etoposide treatment. These results suggest that Bax plays an important role for drug-induced thrombocytopenia, and BIP and its derivatives may be utilized to attenuate chemotherapy-induced thrombocytopenia.

We demonstrated that (1) BIP is cell-permeable in a megakaryocytic cell line (Dami cells) and primary cultured mouse megakaryocytes, (2) BIP suppressed anti-cancer drug-induced apoptosis in these cell types, and (3) BIP did not interfere the production of Integrin αIIB positive particle (platelet like particle) by primary cultured mouse megakaryocytes. Our findings show Bax plays a key role in the chemotherapy-induced apoptosis of megakaryocytes, and that BIP is useful therapeutic to protect megakaryocytes from the toxicity of chemotherapy.

The present study showed the effectiveness of BIP in cultured megakaryocytes. Importantly, we also obtained a preliminary result showing that BIP pre-treatment attenuated Etoposide-induced platelet decrease in mouse model. To develop the technology protecting megakaryocytes from chemotherapy, further extensive animal studies are needed. At present, our preliminary study showed that BIP did not show any toxicity in mice even at very high doses. We examined doses of 166.5 mg/kg by i.p. and 16.5 mg/kg by i.v.t. The mice treated by BIP at these doses did not show any sign of illness and lived more than 3 months after the injection. The dose of 166.5 mg/kg is expected to achieve 300 μM of BIP in whole mouse body, if a mouse body is assumed to be filled with water. Probably, much less amount of BIP is sufficient to achieve effective doses (50-400 μM) (Sawada, M., P. Hayes, and S. Matsuyama, *Cytoprotective membrane-permeable peptides designed from the Bax-binding domain of Ku*70. Nat Cell Biol, 2003. 5(4): p. 352-7; Yoshida, T., et al., *Bax-inhibiting peptide derived from mouse and rat Ku*70. Biochem Biophys Res Commun, 2004. 321(4): p. 961-6; Yu, L. Y., et al., *GDNF-deprived sympathetic neurons die via a novel non-mitochondrial pathway*. J Cell Biol, 2003. 163(5): p. 987-97; Qin, Q., K. Patil, and S. C. Sharma, *The role of Bax-inhibiting peptide in retinal ganglion cell apoptosis after optic nerve transection*. Neurosci Lett, 2004. 372(1-2): p. 17-21) in blood or a specific tissue.

Having described the invention, the following is claimed:

1. A method of treating chemotherapy-induced thrombocytopenia, the method comprising:
administering to a subject undergoing chemotherapy a therapeutically effective amount of a Bax-inhibiting peptide, the peptide consisting of the following formula: $X^1PX^2LX^3X^4$ (SEQ ID NO: 7), wherein $X^1$ is selected from amino acids with non-polar side chain; $X^2$ is selected from amino acids with non-polar side chain; $X^3$ is selected from amino acids with charged polar side chain; $X^4$ is selected from amino acids with charged polar side chain; and either $X^1$ or $X^4$ may be absent.

2. The method of claim 1, the therapeutically effective amount of Bax-inhibiting peptide being an amount effective to mitigate chemotherapy induced apoptosis of megakaryocytes of the subject without substantially inhibiting platelet formation of the megakaryocytes.

3. The method of claim 1, the peptide being selected from the group consisting of VPMLKE (SEQ ID NO: 1), VPMLK (SEQ ID NO: 2), PMLKE (SEQ ID NO: 3), PMLK (SEQ ID NO: 4), VPTLK (SEQ ID NO: 5), and VPALR (SEQ ID NO: 6).

4. The method of claim 1, the peptide consisting of VPTLK (SEQ ID NO: 5).

5. The method of claim 1, further comprising administering a therapeutically effective amount of thrombopoeitin (TPO) to the subject.

6. The method of claim 1, the peptide being a cell membrane permeable peptide, which is capable of crossing a megakaryocyte cell membrane without the use of a cell delivery system.

7. A method of treating chemotherapy-induced thrombocytopenia, the method comprising:
administering to a subject undergoing chemotherapy a therapeutically effective amount of a Bax-inhibiting peptide, the peptide being selected from the group consisting of VPMLKE (SEQ ID NO: 1), VPMLK (SEQ ID NO: 2), PMLKE (SEQ ID NO: 3), PMLK (SEQ ID NO: 4), VPTLK (SEQ ID NO: 5), and VPALR (SEQ ID NO: 6).

8. The method of claim 7, the therapeutically effective amount of Bax-inhibiting peptide being an amount effective to mitigate chemotherapy induced apoptosis of megakaryocytes of the subject without substantially inhibiting platelet formation of the megakaryocytes.

9. The method of claim 7, the peptide consisting of VPTLK (SEQ ID NO: 5).

* * * * *

SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

```
<400> SEQUENCE: 1

Val Pro Met Leu Lys Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Val Pro Met Leu Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Pro Met Leu Lys Glu
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Pro Met Leu Lys
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Val Pro Thr Leu Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Pro Ala Leu Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
```

```
<223> OTHER INFORMATION: X is an amino acid with non-polar side chain
<220> FEATURE:
<221> NAME/KEY: X
<222> LOCATION: (3)..(3)
<223> OTHER INFORMATION: X is an amino acid with non-polar side chain
<220> FEATURE:
<221> NAME/KEY: X
<222> LOCATION: (5)..(6)
<223> OTHER INFORMATION: X is an amino acid with with charged polar side
      chain

<400> SEQUENCE: 7

Xaa Pro Xaa Leu Xaa Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Lys Leu Pro Val Met
1               5
```